(12) United States Patent
Sugiura et al.

(10) Patent No.: US 6,361,980 B2
(45) Date of Patent: Mar. 26, 2002

(54) PREPARATION PROCESS OF DIGLYCERIDE

(75) Inventors: Masakatsu Sugiura; Hiroaki Yamaguchi; Naoto Yamada, all of Kashima-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/725,571

(22) Filed: Nov. 30, 2000

(30) Foreign Application Priority Data

Dec. 17, 1999 (JP) ............................ 11-359794

(51) Int. Cl.$^7$ .............................. C12P 7/64; C12P 7/62; C12P 7/40; C12P 7/24; C12P 7/02; C07C 51/00
(52) U.S. Cl. ................ 435/134; 435/135; 435/136; 435/147; 435/155; 554/124; 554/161; 554/163; 554/167; 554/168; 554/170; 554/172; 554/173
(58) Field of Search .................. 435/134, 135, 435/136, 147, 155; 554/124, 168, 173, 161, 163, 167, 170, 172

(56) References Cited

FOREIGN PATENT DOCUMENTS

| EP | 0 307 154 | 3/1989 |
|----|-----------|--------|
| JP | 64-71495 | 3/1989 |
| JP | 04-330289 | 11/1992 |
| JP | 4-330289 | 11/1992 |
| JP | 10-234391 | 9/1998 |
| JP | 10234391 A * | 9/1998 |

OTHER PUBLICATIONS

T. Luck, et al., Chemical Abstracts, DN 114:162415, "Lipase–Catalyzed Interesterification of Triglycerides in a Solvent–Free Process", 1991 (English Abstract only).

* cited by examiner

Primary Examiner—Samuel Barts
Assistant Examiner—Elvis O. Price
(74) Attorney, Agent, or Firm—Oblon, Spivak, McClelland, Maier & Neustadt, P.C.

(57) ABSTRACT

The present invention provides a process for preparing a diglyceride, which includes:

in an enzyme-packed tower which includes an immobilized lipase preparation, carrying out an esterification reaction between:
  (1) an acyl group donor selected from the group including a fatty acid, a lower alcohol ester thereof, and a mixture thereof; and
  (2) an acyl group acceptor selected from the group including glycerol, a monoglyceride, and a mixture thereof;
to obtain a reaction fluid from the enzyme-packed tower;
reducing a water content or a lower alcohol content in the reaction fluid; and
subsequent to the reducing, recirculating the reaction fluid to the enzyme-packed tower, wherein a residence time of the reaction fluid in the enzyme-packed tower is 120 seconds or less;
to obtain a diglyceride. According to the present invention, a high-purity glyceride can be provided at a high yield in a short period of time.

15 Claims, 1 Drawing Sheet

PREPARATION PROCESS OF DIGLYCERIDE

BACKGROUND OF THE INVENTION

1. Field of the Invention

The present invention relates to a process for preparing a high-purity glyceride at a high yield in a short period of time.

2. Description of the Background Art

Glycerides are used as base materials in fields of cosmetics, drugs, etc., and as additives for improving plasticity of oils and fats and edible oils in a field of food. Such glycerides are generally prepared by an esterification reaction of glycerol with its corresponding fatty acid, an alcohol interchange reaction of glycerol with oil or fat, or the like. These preparation processes are roughly divided into chemical reaction processes, which make use of an alkali catalyst or the like, and biochemical reaction processes, which make use of a fat-hydrolyzing enzyme such as a lipase, or the like. However, the biochemical reaction processes are more generally used from the viewpoints of the yield and purity of the glycerides synthesized and the energy savings.

Conventional biochemical reaction processes include processes in which a fatty acid or the like is reacted with glycerol in the presence of a 1,3-position-selective lipase while removing water formed by the reaction outside the system, thereby obtaining a diglyceride at high yield and purity (Japanese Patent Application Laid-Open No. 71495/1989); processes in which glycerol is added in an equimolar amount or more to a fatty acid to react them, the reaction is stopped when the concentration of a diglyceride has been enhanced, insoluble glycerol is separated, and the reaction is further conducted while dehydrating, thereby synthesizing the diglyceride at a high esterification reaction rate by improving dehydration efficiency (Japanese Patent Application Laid-Open No. 330289/1992); and processes in which a mixture of a fatty acid or the like and glycerol or the like is reacted in a flow tube type reactor filled with a lipase while controlling the superficial velocity of the mixture in the reactor to at least 0.05 cm/s (Japanese Patent Application Laid-Open No. 234391/1998), etc.

Among the above-described processes, however, the technique described in Japanese Patent Application Laid-Open No. 71495/1989 does not investigate production conditions at an industrial level; the technique described in Japanese Patent Application Laid-Open No. 330289/1992 involves technical difficulties such as necessity of stopping the reaction at the time the concentration of the diglyceride reaches a peak; and the technique described in Japanese Patent Application Laid-Open No. 234391/1998 is easy to operate and can improve the reaction rate to some extent, but is insufficient in the purity of the resulting diglyceride and the industrial scale-up technique.

Accordingly, there is a need for a process for preparing a high-purity glyceride at a high yield in a short period of time at an industrial level.

SUMMARY OF THE INVENTION

It is thus an object of the present to provide a process for preparing a high-purity glyceride at a high yield in a short period of time at an industrial level.

This and other objects of the invention have been achieved by a process for preparing a diglyceride, which includes:

in an enzyme-packed tower which includes an immobilized lipase preparation, carrying out an esterification reaction between:

(1) an acyl group donor selected from the group including a fatty acid, a lower alcohol ester thereof, and a mixture thereof; and (2) an acyl group acceptor selected from the group including glycerol, a monoglyceride, and a mixture thereof;

to obtain a reaction fluid from the enzyme-packed tower;

reducing a water content or a lower alcohol content in the reaction fluid; and subsequent to the reducing, recirculating the reaction fluid to the enzyme-packed tower, wherein a residence time of the reaction fluid in the enzyme-packed tower is 120 seconds or less;

to obtain a diglyceride.

According to the present invention, a high-purity glyceride can be provided at a high yield in a short period of time.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 1:
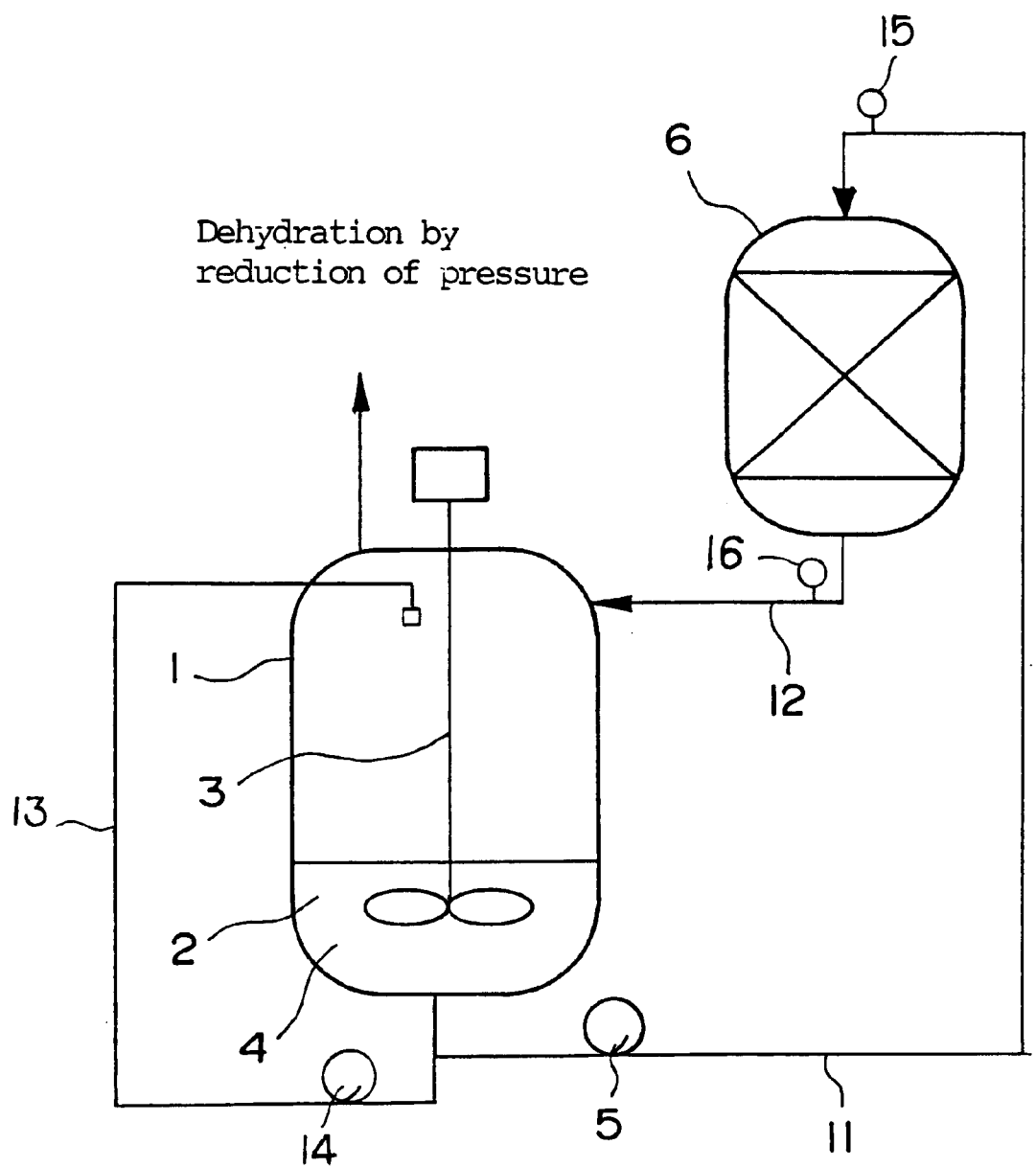
FIG. 1 schematically illustrates a preparation process in the present invention.

In the drawing, the respective reference characters have the following meanings:

1: dehydration tank;

2: mixture of raw materials;

3: stirrer;

4: mixture of diglyceride, by-products, unreacted raw materials and intermediates;

5, 14: pumps;

6: enzyme-packed tower;

11, 12: circulation lines for the enzyme-packed tower;

13: circulation line for the dehydration tank; and

15,16: pressure gauges.

DETAILED DESCRIPTION OF THE PREFERRED EMBODIMENTS

Various other objects, features and attendant advantages of the present invention will be more fully appreciated as the same becomes better understood from the following detailed description of the preferred embodiments of the invention.

The present inventors have made various enzyme-packed towers which are packed with an enzyme in the same amount and different in packing thickness and sectional area to circulate a reaction fluid in the same flow rate, thereby investigate the influence of a superficial velocity on reaction rate and the purity of the resulting diglyceride. However, no change has been observed therebetween. On the other hand, analysis of compositional changes of the reaction fluid in the flowing direction in the interior of each enzyme-packed tower has revealed that the concentration of a 1,3-diglyceride increases in the vicinity of an inlet of the tower, but does not very increase at the lower part from the middle of the tower, and the concentration of a triglyceride increases on the contrary even when a 1,3-position-selective lipase is used. From these facts, the present inventors have found that when residence time is long, the 1,3-position esterification reaction is equilibrated by the influence of water formed by the reaction to inhibit the formation of the intended diglyceride even when a superficial velocity of a reaction fluid in an enzyme-packed tower is high, and on the other hand the concentration of a triglyceride is increased by the progress of a rearrangement reaction from the 1,3-diglyceride into 1,2-diglyceride, which is not affected by the water, and the esterification thereof to incur the lowering of the purity of the diglyceride, and that when the reaction is operated by controlling the residence time to a certain period of time or shorter, a high-purity glyceride is efficiently obtained at an industrial level.

According to the present invention, there is thus provided a process for preparing a diglyceride, which comprises, in an esterification reaction in which a fatty acid or a lower alcohol ester thereof, which is an acyl group donor, and glycerol or a monoglyceride, which is an acyl group acceptor, are fed to an enzyme-packed tower packed with an immobilized lipase preparation to cause a reaction fluid to flow out of the enzyme-packed tower, and a water content or lower alcohol content in the reaction fluid is reduced in a dehydration tank to circulating the reaction fluid to the enzyme-packed tower, conducting the feed of the reaction fluid to the enzyme-packed tower under conditions that residence time amounts to 120 seconds or shorter.

The residence time herein is defined as the time required for the reaction fluid to pass through an enzyme-packed part in the enzyme-packed tower and calculated out by dividing an enzyme packing volume, i.e., a bulk volume (not a void volume of voids in an enzyme preparation) filled with and occupied by the enzyme preparation by a circulating flow rate. In the present invention, the feed of the reaction fluid to the enzyme-packed tower is conducted under conditions that the residence time amounts to 120 seconds or shorter, preferably 10 to 80 seconds, more preferably 20 to 50 seconds, thereby permitting preparing a high-purity diglyceride at an industrial level and a high production rate. If the reaction is conducted under such conditions that the residence time exceeds 120 seconds, the purity of the diglyceride is lowered due to increase in the concentration of a triglyceride formed.

Preferably, the reaction in the present invention is conducted while decreasing water or a lower alcohol formed by the reaction in a dehydration tank. In the present invention, it is preferred from the viewpoint of enhancing the purity and production rate of the diglyceride that the dehydration or dealcoholization of the reaction fluid be conducted under conditions that a volumetric mass transfer coefficient $k_L a$ (wherein $k_L$ is a mass transfer coefficient, and a is a gas-liquid interfacial mass transfer area per unit volume) amounts to at least 0.0005 ($s^{-1}$), preferably 0.0008 to 0.01 ($s^{-1}$) in addition to the conditions of the residence time in the enzyme-packed tower.

In a batch-wise reactor of gram level, the volume of a dehydration tank may also be small, and the whole reaction mixture in the dehydration tank becomes a high vacuum state, thereby permitting dehydration in the whole area of the reaction mixture even by stirring alone. However, in a batch-wise reactor at a level of several tens kilograms to tons, high vacuum cannot be achieved in the interior of the reaction mixture due to the own weight of the reaction mixture in a dehydration tank even when the space area of the dehydration tank is in the highest vacuum, and the dehydration rate becomes insufficient because no dehydration from the interior of the reaction mixture occurs. Therefore, the present inventors have found that it is preferred that the volumetric mass transfer coefficient $k_L a$ be controlled to a certain value or higher in such a reactor of industrial level in that the viewpoint dehydration can be efficiently conducted, so that the above-described inhibition of 1,3-position esterification reaction by water can be avoided, and a high-purity diglyceride can be prepared at a high production rate. From such a point of view, it is preferred that the feed of the reaction fluid to the dehydration tank be conducted by means of a spray nozzle and adjusted so as to give an average droplet diameter of at most 5 mm, more preferably at most 2 mm.

The $k_L a$ value may be calculated out either by the analysis of a dehydration rate in the reaction or by determining only a dehydration rate under the same dehydration conditions irrespective of reaction. For example, a water content $[H_2O]$ in the reaction fluid within the dehydration tank is determined with time. Supposing that a water content after a sufficient period of time has elapsed is an equilibrium water content $[H_2O]^*$, and the time is t, a dehydration rate equation is represented by $d[H_2O]/dt=-k_L a([H_2O]-[H_2O]^*)$. This equation is integrated to give $\ln([H_2O]-[H_2O]^*)=-k_L a \cdot t + \text{constant}$. Accordingly, since $\ln([H_2O]-[H_2O]^*)$ has linearity to the time, the slope ($k_L a$) of this straight line may be found by the method of least squares.

Preferable examples of a method for the dehydration or dealcoholization of the reaction fluid include reduction of pressure, passing a dry inert gas, and using a water absorbent such as a molecular sieve. Among these methods, reduction of pressure is preferred in that the operation can be performed at a low temperature, and there is no need to recover both inert gas and dehydrating agent. The degree of vacuum is preferably 70 hPa or lower, more preferably 15 hPa or lower. No particular limitation is imposed on the form, size and number of dehydration tanks. The superficial velocity is preferably not lower than 1 mm/s, more preferably higher than 2 mm/s because the mass transfer resistance between solid and liquid becomes great to slow a reaction rate when the superficial velocity is too low.

As conditions of the interior of the enzyme-packed tower, defined as $L/d^2$, wherein L is a packing thickness (m) in a flowing direction within the tower, and d is an average particle diameter (mm) of an enzyme preparation, is preferably controlled to at most 25, more preferably at most 20, more particularly preferably at most 15, most preferably at most 10, and most particularly preferably at most 3. This means "$L/d^2$" derived out on the basis of the Kozeny-Carman's equation:

$$\Delta P = \text{constant} \times u \times L / d^2$$

wherein $\Delta P$ is a pressure drop of the enzyme-packed tower, u is a superficial velocity, L is a packing thickness in a flowing direction within the enzyme-packed tower, and d is an average particle diameter of an enzyme preparation, for calculating out the pressure drop of the enzyme-packed tower.

In order to meet the above conditions, an enzyme preparation having an average particle diameter d of at least 0.1 mm, and more preferably 0.2 to 0.8 mm, is preferably used as the immobilized lipase preparation. The packing thickness L of the enzyme is preferably preset so as to be at most 1 m, and more preferably 0.05 to 0.6 m. These factors are not important in a small-scale reactor of laboratory level, but important in a large-scale reactor of industrial level.

The operation is preferably conducted under conditions that the pressure drop of the enzyme-packed tower is 20 $kg/cm^2$ or smaller, and more preferably 10 $kg/cm^2$ or smaller because plant cost can be reduced from the viewpoints of design strength of the enzyme-packed tower and load against a circulating pump. When the reaction is conducted repeatedly under a high pressure, there is a possibility that the immobilized enzyme may be compacted to increase the pressure drop, or the activity of the enzyme may be deteriorated to elongate the reaction time.

Preferable examples of the acyl group donor which is a raw material for the reaction, i.e., a fatty acid or a lower alcohol ester thereof, include saturated or unsaturated fatty acids having 2 to 24 carbon atoms, for example, butyric acid, valeric acid, capronic acid, enanthic acid, caprylic acid, pelargonic acid, capric acid, undecanoic acid, lauric acid, myristic acid, palmitic acid, zoomaric acid, stearic acid, oleic acid, elaidic acid, linoleic acid, arachidonic acid, gadoleic acid, arachic acid, behenic acid and erucic acid, and besides higher unsaturated fatty acids such as eicosapentaenoic acid, docosahexaenoic acid and -linolenic acid; fatty acids derived from animal and vegetable oils such as rapeseed oil, soybean oil, cotton-seed oil, olive oil, corn oil, coconut oil, palm oil, perilla oil, linseed oil, borage oil, beef tallow, lard and fish oil; fatty acids obtained by processing these fatty acids by a means such as hardening, distillation or fractionation, and lower alcohol esters of these fatty acids. Examples of the lower alcohol esters include esters with a lower alcohol having 1 to 3 carbon atoms, i.e., methanol, ethanol, propanol or 2-propanol. These acyl group donors may be used either singly or in any combination thereof.

As the acyl group acceptor which is another raw material for the reaction, i.e., glycerol, may be used a commercially available product. No particular limitation is imposed on a mixing ratio of the acyl group donor to the acyl group acceptor. However, the acyl group of the acyl group donor is preferably present within a range of at least 1 mol, and more preferably 1.6 to 2.8 mol, per mol of a glyceryl group of the acyl group acceptor.

A monoglyceride may be added to the mixture of the raw materials. Even when glycerol is mixed with the fatty acid or the like, the reaction becomes a heterogeneous reaction in which a fatty acid phase and a glycerol phase are present, since mutual solubility between the raw materials is low. When the monoglyceride is added, however, the solubility of glycerol in the fatty acid phase becomes high from the initial stage of the reaction, so that the reaction rate is enhanced.

As the immobilized enzyme preparation used in the present invention, is preferred an enzyme (hereinafter referred to as "immobilized, 1,3-position-selective lipase") specifically acting on the 1- and 3-positions of glycerol. Preferable examples of such a 1,3-position-selective lipase include lipases derived from microorganisms of the genera Rhizopus, Aspergillus and Mucor, and splenic lipases, more specifically, lipases derived from *Rhizopus delemar, Rhizopus japonicus, Rhizopus niveus, Aspergillus niger, Mucor javanicus* and *Mucor miehei*. The immobilized lipase preparation is obtained by immobilizing a lipase in accordance with a publicly known method for immobilizing an enzyme, for example, a method described in "Immobilized Enzymes", edited by Ichiro Senhata, published by Kodansha, pages 9 to 85, or "Immobilized Biocatalysts", edited by Ichiro Senhata, published by Kodansha, pages 12 to 101. The immobilized lipase preparation must exhibit water-holding capacity to keep its properties under conditions of reduced pressure. In order to meet such a requirement, a lipase immobilized on an ion-exchange resin is particularly preferred. The esterification activity of the immobilized lipase preparation is preferably at least 100 (unit/g-enzyme), particularly at least 200 (unit/g-enzyme). Commercially-available immobilized 1,3-position-selective lipases include "Lipozyme IM" (trade name, product of Novo Nordisk Bioindustry Co.).

Preferably, a solvent such as hexane, octane or petroleum ether may also be used in the reaction of the acyl group donor with the acyl group acceptor in the present invention. However, in view of its removal and purification, it is preferred that no solvent be added. In order to inhibit hydrolysis, it is also preferred that no any other water than water dissolved in the lipase preparation and raw materials for the reaction be added to the reaction system. The reaction temperature in the present invention is preferably 20 to 100° C., particularly 35 to 70° C.

Unreacted glycerol, fatty acid and/or lower alcohol ester of the fatty acid, and monoglyceride contained in the reaction mixture after completion of the reaction can be easily removed by a conventionally well-known, isolating and purifying means such as molecular distillation. However, a triglyceride and a diglyceride are difficult to be separated from each other on an industrial level. Accordingly, the purity of the resulting diglyceride and the yield of reaction can be represented by the expressions D/(D+T) and D+T, respectively. In the expressions, D is a diglyceride concentration in the reaction product, and T is a triglyceride concentration in the reaction product.

A preparation process of a diglyceride in the present invention is exemplified as illustrated in, for example, FIG. 1. A mixture 2 of raw materials is placed in a dehydration tank 1 and fed to an enzyme-packed tower 6 through a line 11 by means of a pump 5 while suitably stirring the mixture 2 by a stirrer 3 (in this step, the feed of the mixture to the enzyme-packed tower is conducted under such conditions that the residence time amounts to 120 seconds or shorter). A mixture 4 of a diglyceride formed by a reaction within the enzyme-packed tower 6, by-products and unreacted raw materials is entered into the dehydration tank 1 through a line 12 (Although the dehydration of the mixture is preferably conducted under conditions that a volumetric mass transfer coefficient $K_L a$ is at least 0.0005 ($s^{-1}$), this requirement is realized by using a spray nozzle in the feed of the reaction fluid to the dehydration tank 1 through a line 13 by means of a pump 14.). The above process is conducted repeatedly, thereby increasing the concentration of the diglyceride. The dehydration tank 1 is kept under reduced pressure during this process to remove water and the like formed by the reaction for forming the diglyceride.

EXAMPLES

Having generally described this invention, a further understanding can be obtained by reference to certain specific examples which are provided herein for purposes of illustration only and are not intended to be limiting unless otherwise specified.

In the following Examples, the volumetric mass transfer coefficient $k_L a$ was calculated out by the method of least squares in accordance with the above-described method, in which an oil obtained after completion of the reaction in an amount equal to a batch size was adjusted in such a manner that a water content is about 0.5%, and the oil was charged into the dehydration tank to conduct circulation on the spray side at the same flow rate as that in each Example or Comparative Example without conducting the circulation to the enzyme-packed tower, thereby determining a water content [$H_2O$] with time under reduced pressure and regarding a water content after 10 hours as an equilibrium water content [$H_2O$]*.

The enzymatic activity was calculated out from a consumption rate of a fatty acid and an amount of an immobilized enzyme used as determined from the concentration of oleic acid at the time a reaction is started and after 15 minutes by placing oleic acid (86 g), glycerol (14 g) and the immobilized enzyme (5 g) in a 4-necked flask and stirring the contents at 300 rpm to conduct the reaction at 40° C. and 6.7 hPa with an activity unit that consumes 1 μmol of oleic acid for 1 minute regarded as 1 unit.

Example 1

A reactor used was composed of an enzyme-packed tower (enzyme packing volume: 0.0132 m$^3$; bulk specific gravity of the preparation: 0.38 g/cc) packed with a 1,3-position-selective, immobilized lipase, Lipozyme IM (product of Novo Nordisk Bioindustry Co.; 300 unit/g enzyme; 5 kg) and a dehydration tank for conducting dehydration by reduction of pressure. The dehydration tank was charged with oleic acid (86 kg) and glycerol (14 kg), and the temperature of the reactants was preset to 40° C. with stirring. The feed of the reaction fluid to the enzyme-packed tower and the spray nozzle of the dehydration tank was then started, and the interior of the dehydration tank was controlled so as to give a degree of vacuum of 6.7 hPa by means of a vacuum pump. The feed flow rate of the reaction fluid to the enzyme-packed tower was controlled to 1.2 m3/hr, and a value (residence time) obtained by dividing the enzyme packing volume by the flow rate was adjusted so as to be 40 seconds. The circulating flow rate to the spray nozzle was determined to be 1.2 m$^3$/hr.

After a part of an oil obtained by the reaction was taken out after 3.5 hours from the beginning of the reaction to determine the amount of the fatty acid by alkalimetry, followed by trimethylsilylation, the composition of a triglyceride, diglyceride and monoglyceride was found by gas chromatography. The result thereof is shown in Table 1.

Incidentally, the pressure drop is a difference between numerical values read by pressure gauges provided at the inlet and outlet of the enzyme-packed tower, respectively, the enzyme packing thickness is a distance over which the enzyme preparation is packed in a flowing direction of the reaction fluid within the enzyme-packed tower, the superficial velocity is a numerical value obtained by dividing the flow rate to the enzyme-packed tower by a sectional area of the packed tower in a direction perpendicular to the flowing direction.

Example 2

An operation was conducted in the same manner as in Example 1 except that the flow rate of the reaction fluid to the enzyme-packed tower was changed to 0.6 m$^3$/hr, so as to find the composition. The results are shown in Table 1.

Example 3

An operation was conducted in the same manner as in Example 1 except that the flow rate on the spray side was changed to 0.3 m$^3$/hr, so as to find the composition. The result thereof is shown in Table 1.

Comparative Example 1

An operation was conducted in the same manner as in Example 1 except that the flow rate of the reaction fluid to the enzyme-packed tower was changed to 0.3 m$^3$/hr, so as to find the composition. The result thereof is shown in Table 1.

Comparative Example 2

An operation was conducted in the same manner as in Example 1 except that the packing amount of the enzyme was increased to 4 times, and the flow rate of the reaction fluid to the enzyme-packed tower was changed to 1 m$^3$/hr because the pressure drop of the enzyme-packed tower increased, so as to find the composition. The result thereof is shown in Table 1.

Comparative Example 3

An operation was conducted in the same manner as in Example 1 except that the 1,3-position-selective, immobilized lipase, Lipozyme IM was ground in a mortar to make the particle diameter thereof small, and the flow rate of the reaction fluid to the enzyme-packed tower was changed to 0.14 m$^3$/hr, so as to find the composition. The result thereof is shown in Table 1.

Comparative Example 4

A reactor of laboratory level was used to feed a reaction fluid at a circulating flow rate of 96 ml/min to an enzyme-packed tower under conditions that the packing amount of the 1,3-position-selective, immobilized lipase, Lipozyme IM was 100 g, and a batch size was 1 kg, thereby conducting a reaction without conducting circulation on the spray side to find the composition. The result thereof is shown in Table 1.

TABLE 1

|  | Example | | | Comparative Example | | | |
| --- | --- | --- | --- | --- | --- | --- | --- |
|  | 1 | 2 | 3 | 1 | 2 | 3 | 4*1 |
| Batch size (kg) | 100 | 100 | 100 | 100 | 100 | 100 | 1 |
| Oleic acid (kg) | 86 | 86 | 86 | 86 | 86 | 86 | 0.86 |
| Glycerol (kg) | 14 | 14 | 14 | 14 | 14 | 14 | 0.14 |
| Immobilized enzyme | IM$^{+2}$ | IM$^{+3}$ | IM$^{+2}$ | IM$^{+2}$ | IM$^{+2}$ | IM$^{+2}$ | IM$^{+2}$ |
| Average particle diameter d (mm) | 0.43 | 0.43 | 0.43 | 0.43 | 0.43 | 0.08 | 0.43 |
| Amount (kg) | 5 | 5 | 5 | 5 | 20 | 5 | 0.1 |
| Packing thickness | 0.18 | 0.18 | 0.18 | 0.18 | 0.7 | 0.18 | 0.33 |
| Superficial velocity U (mm/s) | 4.4 | 2.2 | 4.4 | 1.1 | 3.7 | 0.5 | 2.0 |
| Residence time (s) | 40 | 79 | 40 | 158 | 190 | 351 | 164 |
| =L/d$^2$ | 0.95 | 0.95 | 0.95 | 0.95 | 3.80 | 27.50 | 1.80 |
| Pressure loss P (kg/cm$^2$) | 2.6 | 1.5 | 2.6 | 0.7 | 9.5 | 8.5 | 2.5 |
| Spray nozzle | Used | Used | Used | Used | Used | Used | Not used |
| Droplet diameter (mm) | 1 | 1 | 1.2 | 1 | 1 | 1 | — |
| Circulation on spray | 1.2 | 1.2 | 0.3 | 1.2 | 1.2 | 1.2 | 0 |

TABLE 1-continued

|  | Example | | | Comparative Example | | | |
| --- | --- | --- | --- | --- | --- | --- | --- |
|  | 1 | 2 | 3 | 1 | 2 | 3 | 4*1 |
| side (m³/hr) |  |  |  |  |  |  |  |
| $k_L a$ (s⁻¹) | 0.0017 | 0.0017 | 0.0005 | 0.0017 | 0.0017 | 0.0017 | 0.0007 |
| Reaction time (hr) | 3.5 | 3.5 | 3.5 | 3.5 | 3.5 | 3.5 | 7.0 |
| Reaction product (wt %) |  |  |  |  |  |  |  |
| Oleic acid | 14.1 | 15.4 | 16.4 | 43.1 | 11.6 | 47.8 | 41.9 | 12.4 |
| Glycerol | 0.3 | 0.7 | 0.5 | 2.1 | 0.4 | 2.7 | 1.7 | 0.1 |
| Monoglyceride (M) | 14.1 | 18.3 | 16.8 | 15.3 | 15.0 | 16.4 | 15.4 | 9.3 |
| Diglyceride (D) | 65.6 | 58.1 | 59.5 | 32.8 | 55.7 | 26.8 | 33.1 | 63.0 |
| Triglyceride (T) | 5.9 | 7.5 | 6.8 | 6.7 | 17.3 | 6.3 | 7.9 | 15.2 |
| Total | 100.0 | 100.0 | 100.0 | 100.0 | 100.0 | 100.0 | 100.0 | 100.0 |
| Yield of reaction D + T (wt. %) | 71.5 | 65.6 | 66.3 | 39.5 | 73.0 | 33.1 | 41.0 | 78.2 |
| Purity of diglyceride D/(D + T) (wt %) | 91.7 | 88.6 | 89.7 | 83.0 | 76.3 | 80.9 | 80.7 | 80.6 |

*1: Example 2 of Japanese Patent Application Laid-Open No. 234391/1998.
*2: Lipozyme IM (product of Novo Nordisk Bioindustry Co.).

Each of the above references, patents, applications and published is hereby incorporated by reference, the same as if set forth at length.

This application is based on Japanese Patent Application No. 359794/1999, filed Dec. 17, 1999, the entire contents of which are hereby incorporated by reference.

Having now fully described this invention, it will be apparent to one of ordinary skill in the art that many changes and modifications can be made thereto without departing from the spirit or scope of the invention as set forth herein.

What is claimed is:

1. A process for preparing a diglyceride, comprising:
   in an enzyme-packed tower comprising an immobilized lipase preparation, carrying out an esterification reaction between:
   (1) an acyl group donor selected from the group consisting of a fatty acid, a lower alcohol ester thereof, and a mixture thereof; and
   (2) an acyl group acceptor selected from the group consisting of glycerol, a monoglyceride, and a mixture thereof;
   to obtain a reaction fluid from said enzyme-packed tower;
   reducing a water content or a lower alcohol content in said reaction fluid; and
   subsequent to said reducing, recirculating the reaction fluid to said enzyme-packed tower, wherein a residence time of said reaction fluid in said enzyme-packed tower is 120 second or less;
   to obtain a diglyceride,
   wherein said reducing comprises dehydrating or dealcoholizing said reaction fluid is by feeding said reaction fluid through a spray nozzle, in a dehydration process.

2. The process according to claim 1, wherein said reducing comprises dehydrating or dealcoholizing said reaction fluid under conditions that a volumetric mass transfer coefficient $k_L a$ (wherein $k_L$ is a mass transfer coefficient, and a is a gas-liquid interfacial mass transfer area per unit volume) is at least 0.0005 (s⁻¹).

3. The process according to claim 1, wherein said reducing is carried out in a dehydration tank.

4. The process according to claim 1, wherein said immobilized lipase preparation comprises an immobilized, 1,3-position-selective lipase having an esterification activity of at least 100 (unit/g-enzyme).

5. The process according to claim 1, wherein, in said esterification reaction, the following condition is satisfied:

$$L/d^2 \leq 25$$

wherein L is a packing thickness (m) in a flowing direction in said enzyme-packed tower, and d is an average particle diameter (mm) of said immobilized lipase preparation.

6. The process according to claim 5, wherein said average particle diameter d is at least 0.1 mm.

7. The process according to claim 1, wherein a pressure loss of said enzyme-packed tower is 20 kg/cm² or smaller.

8. The process according to claim 1, wherein said fatty acid is an saturated or unsaturated fatty acid having 2 to 24 carbon atoms.

9. The process according to claim 1, wherein said fatty acid is selected from the group consisting of saturated or unsaturated fatty acids having 2 to 24 carbon atoms, butyric acid, valeric acid, capronic acid, enanthic acid, caprylic acid, pelargonic acid, capric acid, undecanoic acid, lauric acid, myristic acid, palmitic acid, zoomaric acid, stearic acid, oleic acid, elaidic acid, linoleic acid, arachidonic acid, gadoleic acid, arachic acid, behenic acid, erucic acid, eicosapentaenoic acid, docosahexaenoic acid, -linolenic acid; fatty acids derived from animal and vegetable oils, rapseed oil, soybean oil, cotton-seed oil, olive oil, corn oil, coconut oil, palm oil, perilla oil, linseed oil, borage oil, beef tallow, lard and fish oil; fatty acids obtained by processing fatty acids hardening, distillation or fractionation; and mixtures thereof.

10. The process according to claim 1, wherein said lower alcohol ester thereof is a lower alcohol ester of a fatty acid selected from the group consisting of saturated or unsaturated fatty acids having 2 to 24 carbon atoms, butyric acid, valeric acid, capronic acid, enanthic acid, caprylic acid, pelargonic acid, capric acid, undecanoic acid, lauric acid, myristic acid, palmitic acid, zoomaric acid, stearic acid, oleic acid, elaidic acid, linoleic acid, arachidonic acid, gadoleic acid, arachic acid, behenic acid, erucic acid, eicosapentaenoic acid, docosahexaenoic acid, -linolenic acid; fatty acids derived from animal and vegetable oils, rapseed oil, soybean oil, cotton-seed oil, olive oil, corn oil, coconut oil, palm oil, perilla oil, linseed oil, borage oil, beef tallow, lard and fish oil; fatty acids obtained by processing fatty acids hardening, distillation or fractionation; and mixtures thereof.

11. The process according to claim 1, wherein said lower alcohol ester thereof is selected from the group consisting of esters with a lower alcohol having 1 to 3 carbon atoms, methanol, ethanol, propanol, 2-propanol, and mixtures thereof.

12. The process according to claim 1, wherein said acyl group donor is present in an amount ranging from at least 1 mol per mol of a glyceryl group of said acyl group acceptor.

13. The process according to claim 1, wherein said esterification reaction is carried out in the presence of a monoglyceride.

14. The process according to claim 1, wherein said immobilized enzyme preparation comprises an immobilized, 1,3-position-selective lipase is selected from the group consisting of lipases derived from microorganisms of the genera Rhizopus, Aspergillus and Mucor, splenic lipases, lipases derived from *Rhizopus delemar, Rhizopus japonicus, Rhizopus niveus, Aspergillus niger, Mucor javanicus* and *Mucor miehei*.

15. The process according to claim 1, further comprising separating from said diglyceride at least one selected from the group consisting of unreacted glycerol, unreacted fatty acid, unreacted said lower alcohol ester thereof, monoglyceride, and mixtures thereof.

* * * * *

UNITED STATES PATENT AND TRADEMARK OFFICE
CERTIFICATE OF CORRECTION

PATENT NO.   : 6,361,980 B2
DATED        : March 26, 2002
INVENTOR(S)  : Sugiura et al.

It is certified that error appears in the above-identified patent and that said Letters Patent is hereby corrected as shown below:

Column 5,
Line 46, "Rhizopus, Aspergillus", should read -- *Rhizopus, Aspergillus* --.
"Mucor", should read -- *Mucor* --.

Column 12,
Line 5, "Rhizopus, Aspergillus", should read -- *Rhizopus, Aspergillus* --.
"Mucor", should read -- *Mucor* --.

Signed and Sealed this

Eighth Day of October, 2002

*Attest:*

JAMES E. ROGAN
*Attesting Officer*   *Director of the United States Patent and Trademark Office*